United States Patent
Cutie et al.

(10) Patent No.: US 6,780,432 B1
(45) Date of Patent: *Aug. 24, 2004

(54) CORE FORMULATION

(75) Inventors: Anthony J. Cutie, Bridgewater, NJ (US); Akwete L. Adjei, Bridgewater, NJ (US); Frederick A. Sexton, Fair Haven, NJ (US)

(73) Assignee: Aeropharm Technology, Inc., Edison, NJ (US)

( * ) Notice: Subject to any disclaimer, the term of this patent is extended or adjusted under 35 U.S.C. 154(b) by 286 days.

This patent is subject to a terminal disclaimer.

(21) Appl. No.: 09/702,263

(22) Filed: Oct. 31, 2000

Related U.S. Application Data

(60) Provisional application No. 60/201,057, filed on May 1, 2000.

(51) Int. Cl.[7] .............................. A61K 9/22; A61K 9/36; A61K 9/16
(52) U.S. Cl. .................. 424/468; 424/479; 424/490
(58) Field of Search ......................... 514/369

(56) References Cited

U.S. PATENT DOCUMENTS

| | | | | |
|---|---|---|---|---|
| 6,011,049 A | * | 1/2000 | Whitcomb | 514/369 |
| 6,153,632 A | * | 11/2000 | Rieveley | 514/369 |
| 6,197,340 B1 | | 3/2001 | Byrd et al. | 424/468 |

* cited by examiner

*Primary Examiner*—Thurman K. Page
*Assistant Examiner*—Konata M. George
(74) *Attorney, Agent, or Firm*—Karen J. Messick

(57) ABSTRACT

This invention relates to a combination drug product comprising pioglitazone hydrochloride and a biguamide, e.g. metformin. In particular, the product comprises a core of the biguamide, e.g. metformin, at least a portion thereof has a layer or coat thereon of pioglitazone.

15 Claims, No Drawings

CORE FORMULATION

This application claims priority from U.S. provisional application Serial No. 60/201,057 filed May 1, 2000, which is incorporated herein by reference.

BACKGROUND OF THE INVENTION

1. Field of the Invention

This invention relates to a core formulation, and, more particularly, to a core formulation comprising a first layer comprising pioglitazone, which covers at least a portion of a core comprising the biguamide, metformin (i.e., glucophage).

2. Description of the Related Art

Metformin and pioglitazone, or their salts such as the hydrochlorides, maleates, tartrates, etc., are two active ingredients of anti-diabetic drugs that are used to treat diabetic patients, e.g. human beings. These two active agents are administered orally to patients in need thereof in protocols calling for the single administration of either ingredient. Heretofore, there has not been revealed or hinted at combining both ingredients and certainly not a physically combined core formulation comprising both ingredients. The use of such a core formulation is advantageous to patients and prescribers because both medicaments are synergistic to each other in the body when used in the management of blood glucose control, i.e., diabetes.

SUMMARY OF THE INVENTION

This invention relates to a core formulation, and, more particularly, to a core formulation comprising a first layer comprising pioglitazone hydrochloride, which covers at least a portion of a core comprising a biguamide. A typical biguamide is metformin.: It typically is used clinically as a pharmaceutically acceptable salt, preferably the hydrochloride salt. A commercial form of metformin hydrochloride is available as glucophage. Its chemical name is N,N-dimethylimidodicarbonimidic diamide hydrochloride. Metformin hydrochloride is a hydrochloride salt of metformin base, and as used herein, "metformin" means the base compound as well as its pharmaceutically acceptable salts. Metformin is used clinically to manage non-insulin dependent diabetes mellitus or "NIDDM", particularly in patients who are not effectively treated with a sulfonylurea. While it is not chemically related to the sulfonylureas, it is routinely utilized in combination with a sulfonylurea, and has been shown to be synergistic in some cases. Other biguamide such as phenformin, buformin etc. can also be used. Additionally, in the treatment of a diabetic patient the metformin, for example, and the pioglitazone hydrochloride are present in effective amounts to provide such treatment.

DETAILED DESCRIPTION OF THE INVENTION

Metformin is an active ingredient for a commercially available drug employed to treat diabetes mellitus in a host or mammal, e.g. a human being, another animal. The typical daily effective dose for the oral treatment of a mammal, i.e., a human, ranges from 500 mg to 2550 mg. Typically, the dose is a single dose of 500 mg to 850 mg.

Pioglitazone hydrochloride, (ACTOS®), is an active ingredient for a commercially available drug employed to treat diabetes mellitus in a host, e.g. a human being. The typical daily effective dose for the oral administration to a mammal, e.g. a human being, ranges from 15 mg to 45 mg, given as a single dose.

Heretofore, the metformin and pioglitazone hydrochloride have not been administered together to try to improve the effectiveness of either drug, although co-administration of the two has been proposed [Whitcomb; et al., U.S. Pat. No. 6,011,049]. However, a combined form of the drugs, i.e. a single integral unit thereof has not heretofore been reported. The present invention provides such a single integral unit in the form of a core formulation.

As indicated above, the relative concentrations of each drug is such that a first layer comprising metformin is prepared. The first layer covers at least a portion of a core comprising metformin. Depending upon the rate of administration and metabolism of the patient destined to be treated, and the concentrations of each ingredient desired for each drug, the first layer may cover only a portion of the core or encompass the entire core. For example, one quarter of the core to about three fourths of the tablet core. The first layer should comprise pioglitazone hydrochloride because its dose requirement is lower compared to metformin. Additionally, it is slightly non-polar, its solubility rate slower, and its absorption rate thus dependent on its dissolution rate in the contents of the gastrointestinal tract compared with metformin.

It is to be understood, depending upon the rate of administration to the patient desired, either the first layer or the core may contain a mixture of the two active ingredients or both the first layer and the core may contain the two active ingredients with different and varying concentrations of one or both active ingredients.

The first layer of the core comprises pioglitazone hydrochloride in an amount of 0.01% to 20% of the total weight of the core formulation, whereas, the metformin in the core is present in an amount of 10% to 97.5% of the total weight of the core formulation.

Where combinations of the two active ingredients are present in the first layer and/or the core, the amounts of pioglitazone hydrochloride ranges from 1 mg to 45 mg whereas the metformin ranges from 100 mg to 2550 mg.

Finally, it is to be understood that a third pharmacologically active material, e.g. a drug, such as for example sulfonylureas, α-glucosidase inhibitors, meglitinides, and ACE, inhibitors may be employed in an admixture with the active ingredients in the first layer and/or the core.

The alpha-glucosidase inhibitors [Jean-Bernard Ducep et al., U.S. Pat. No. 5,504,078], bisglucosylmoranoline derivatives [UK Patent No. GB 2,088 365 A], and glucosylmoranoline derivatives [European Patent No. 87112480.6] include the following medicaments: 1.5-Dideoxy-4-O (.alpha.,D-glucopyranosyl)-1,5-[6,7-dideoxy-7-D-glucoheptopyranosyl)imino]-D-glucitol; 1.5-Dideoxy-4-O (.alpha.,D-glucopyranosyl)-1,5-[(1-deoxy-D-fruictofuiranosyl)imino]-D-glucitol; 1.5-Dideoxy-4-O (.alpha.,D-glucopyraosyl-1,5-[(4-deoxy-4-D-glucopyranosyl)imino]-D-glucitol; 1.5-Dideoxy-4-O (.alpha.,D-glucopyranosyl)-N-[6-deoxy-1-(6-O-D-glucopyranosyl)-.alpha.-D-glucopyranosyl]-1,5-imino-D-glucitol; 1.5-Dideoxy-4-O(.alpha.,D-glucopyranosyl)-N-[6,7-dideoxy-1-(6-O-D-glucopyranosyl)-7-.alpha.-D-glucoheptopyranosyl]-1,5-imino-D-glucitol; 1.5-Dideoxy-4-O(.alpha.,D-glucopyranosyl)-1,5-[(4-deoxy-4-D-glucopyranosyl)methylimino]-D-glucitol; 1.5-Dideoxy-4-O (.alpha.,D-glucopyranosyl)N-[4-deoxy-1-(4-O-D-glucopyranosyl)-.alpha.-D-glucopyranosyl]-1,5-imino-D-glucitol; 1.5-Dideoxy-4-O(.alpha.,D-glucopyranosyl)-1,5-{[2(1-D-arabinofiranose)ethyl]imino}-D-glucitol; 1.5-Dideoxy-4-O(.alpha.,D-glucopyranbsyl)-N-[4-deoxy-1-(6-

O-D-glucopyranosyl)-.alpha.-D-glucopyranosyl]-1,5-imino-D-glucitol; 1.5-Dideoxy-4-O(.alpha.,D-glucopyranosyl)-N-{[4-deoxy-1-(4-O-D-glucopyranosyl)-4-.alpha.-D-glucopyranosyl]methyl}-1,5-imino-D-glucitol; 1.5-Dideoxy-4-O(.alpha.,D-glucopyranosyl)-N-{[4-deoxy-1-(6-O-D-glucopyranosyl)-4-.alpha.-D-glucopyranosyl]methyl}-1,5-imino-D-glucitol; 1.5-Dideoxy-4-O(.alpha.,D-glucopyranosyl)-1,5-[(6-deoxy-1-O-methyl-6-β-D-glucopyranosyl)-imino-D-glucitol; 1.5-Dideoxy-4-O(.alpha,D-glucopyranosyl)-1,5-[(6,7-dideoxy-1-O-methyl-7-β-D-glucoheptopyranosyl)imino]-D-glucitol; 1.5-Dideoxy-4-O(.alpha.,D-glucopyranosyl)-1,5-[(1-deoxy-2-O-methyl-β-D-fructofulranosyl)imino]-D-glucitol, 1.5-Dideoxy-4-O(.alpha.,D-glucopyranosyl)-1,5-[(4-deoxy-1-O-methyl-4-β-D-glucopyranosyl)imino]-D-glucitol; 1.5-Dideoxy-4-O(.alpha.,D-glucopyranosyl)-N-[6-deoxy-1-(1-O-methyl-6-O-β-D-glucopyranosyl)-.alpha.-D -glucopyranosyl]1,5-imino-D-glucitol; 1.5-Dideoxy-4-O(.alpha.,D-glucopyranosyl)-N-[6,7-dideoxy-1-(1-O-mehyl-6-O-β-D-glucopyranosyl)-7-.alpha-D-glucoheptopyranosyl]-1,5-imino-D-glucitol; 1.5-Dideoxy-4-O(.alpha.,D-glucopyranosyl)-1,5-[(4-deoxy-1-O-methyl-4-β-D-glucopyranosyl)methyylimino]-D-glucitol; 1.5-Dideoxy-4-O(.alpha,D-glucopyranosyl)-N-[4-deoxy-1(1-(-methyl-4-O-8-D-glucopyranosyl)-.alpha.-D-glucopyranosyl]-1,5-imino-D-glucitol; 1.5-Dideoxy-4-O(.alpha.,D-glucopyranosyl)-1,5-{[2-(1-O-methyl-1-β-D-arabinofuranosy)ethyl]imino}-D-glucitoi; 1.5-Dideoxy-4-(.alpha.,D-glucopyranosyl)N-[4-deoxy-1-(1-O-methyl-6-O-β-D-glucbpyranosyl)-.alpha.-D-glucopyranosyl]-1,5-imino-D-glucitol; 1.5-Dieoxy-4-O(.alpha.,D-glucopyranosyl)-N-{[4-deoxy-1-(1-O-methyl-4-O-β-D-gluopyranosyl)-4-.alpha.D-glucopyranosyl]methyl}-1,5-imino-D-glucitol; 1.5-Dideoxy-4-O(.alpha.,D-glucopyranosyl)-N-{[4-deoxy-1-(1-O-methyl-6-O-β-D-glucopyranosyl)-4-.alpha.-D-glucopyranosyl]methyl}-1,5-imino-D-glucitol; 1.5-Dieoxy-6-O(.alpha.D-glucopyranosyl)-1,5-[6,7-dideoxy-7-D-glucoheptopyranosyl)imino]-D-glucitol; 1.5-Dideoxy-6-O(.alpha.,D-glucopyranosyl)-1,5-[(1-deoxy-D-fructofulranosyl)imino]-D-glucitol; 1.5-Dideoxy-6-O(.alpha.,D-glucopyranosyl)-1,5-[(4-deoxy-4-D-glucopyranosyl)imino]-D-glucitol; 1.5-Dideoxy-6-O(.alpha.,D-glucopyranosyl)-N-[6-deoxy-1-(6-O-D-glucopyralosyl)-.alpha.-D-glucopyranosyl]-1,5-imino-D-glucitol; 1.5-Dieoxy-6-O(.alphs.,D-glucopyranosyl)-N-[6,7-dideoxy-1-(6-O-Dglucopyranosyl)-7-.alpha-D.-glucoheptopyranosyl]-1,5-imino-D-glucitol; 1.5-Dideoxy-6-O(.alpha.,D-glucopyranosyl)-1,5-[(4-deoxy-4-D-glucopyranosyl)methylimino]-D-glucitol; 1.5-Dideoxy-6-O(.alpha,D-glucopyranosyl)-N-[4-deoxy-1-(4-O-D-glucopyranosyl)-.alpha.-D-glucopyranosyl]-1,5-imino-D-glucitol; 1.5-Dideoxy-6-O(.alpha.,D-glucopyranosyl)-1,5-{[2(1-D-arabinofuranose)ethyl]imino}-D-glucitol; 1.5-Dideoxy-6-O(.alpha.,D-glucopyranosyl)-N-[4-deoxy-(6-O-D-glucopyranosyl)-.alpha.-D-glucopyranosyl]-1,5-imino-D-glucitol; 1.5-Dideoxy-6-O(.alpha.,D-glucopyranosyl)-N-{[4-deoxy-1-(4-O-D-glucopyranosyl)-4-.alpha.-D-glucopyranosyl]methyl}-1,5-imino-D-glucitol; 1.5-Dideoxy-6-O(.alpha.,D-glucopyranosyl)-N-{[4-deoxy-1-(6-O-D-glucopyranosyl)-4-.alpha.-D-glucopyranosyl]methyl}-1,5-imino-D-glucitol; 1.5-Dideoxy-6-O(.alpha.,D-glucopyranosyl)-1,5-[(6,-deoxy-1-O-methyl-6-β-D-glucopyranosyl)-imino)-D-glucitol; 1.5-Dideoxy-6-O(.alpha.,D-glucopyranosyl)-1,5-[(6,7-dideoxy-1-O-methyl-7-β-D-glucoheptopyranosyl)imino)-D-glucitol; 1.5-Dideoxy-6-O(.alpha.,D-glucopyranosyl)-1,5-[(1-deoxy-2-O-methyl-β-D-fructofuranosyl)imino)-D-glucitol; 1.5-Dideoxy-6-O(.alpha.,D-glucopyranosyl)-1,5-[(4-deoxy-1-O-methyl-4-β-D-glucopyranosyl)imino]-D-glucitol; 1.5-Dideoxy-6-O(.alpha.,D-glucopyranosyl)-N-[6-deoxy-1-(1-O-methyl-4-O-β-D-glucopyranosyl)-.alpha.-D-glucopyranosyl]-1,5-iimino-D-glucitol; 1.5-Dideoxy-6-O(.alpha.,D-glucopyranosyl)-N-[6,7-dideoxy-1-(1-O-methyl-6-O-β-D-glucopyranosyl)-7-.alpha.-D-glucoheptopyranosyl]-1,5-imino-D-glucitol; 1.5-Dideoxy-6-O(.alpha.,D-glucopyranosyl)-1,5-[(4-deoxy-1-O-methyl-4-β-D-glucopyranosyl)methylimino]-D-glucitol; 1.5-Dideoxy-6-O(.alpha.,D-glucopyranosyl)-N-[4-deoxy-1-(1-O-methyl-4-O-β-D-glucopyranosyl)-.alpha-D-glucopyranosyl]-1,5-imino-D-glucitol; 1.5-Dideoxy-6-O(.alpha.,D-glucopyranosyl)-1,5-{[2-(1-O-methyl-1-B-D-arabinofuranosyl)ethyl]imino}-D-glucitol; 1.5-Dideoxy-6-O(.alpha.,D-glucopyranosyl)-N-[4-deoxy-1-(1-O-methyl-6-O-β-D-glucopyranosyl)-.alpha.-D-glucopyranosyl]-1,5-imino-D-glucitol; 1.5-Dideoxy-6-O(.alpha.,D-glucopyranosyl)-N-([4-deoxy-1-(1-O-methyl-4-O-β-D-glucopyranosyl)-4-.alpha.-D-glucopyranosyl]methyl}-1,5-imino-D-glucitol; 1.5-Dideoxy-6-O(.alpha.,D-glucopyranosyl)N-([4-deoxy-1-(1-O-methyl-6-O-β-D-glucopyranosyl)-4-.alpha.-D-glucopyranosyl]methyl}-1,5-imino-D-glucitol;

The list of medicaments includes acid addition salt forms with such inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumnaric, maleic, tartaric, citric, ascorbic, maleic, hydroxymaleic and dihydroxymaleic, benzoic, 2-acetoxybenzoic, mandelic and like acids; and with organic sulfonic acids such as methanesulfonic acid and p-toluenesulfonic acid.

The sulfonylureas are a class of compounds that have been widely employed to treat diabetes. Such compounds are well known, for example as described in U.S. Pat. Nos. 3,454,635; 3,669,966; 2,968,158; 3,501,495; 3,708,486; 3,668,215; 3,654,357; and 3,097,242. Especially preferred sulfonylureas to be employed in the combinations of this invention are glyburide, gliquidone, glipizide, tolbutamide, tolazamide, glisoxepid, chlorpropamide, glibornuride, gliclazide, glimepiride, phenbutamide, and tolcyclamide. Other medicaments, such as, for example an antibiotic, a vitamin, a drug that works on the heart, or in the liver, may be admixed with the active ingredients in the first layer and/or the core.

The resultant core having the first layer thereon is prepared by any conventional means known in the pharmaceutical art, e.g. compression, tabletting technology, spraying technology, or encapsulation in a pharmaceutically acceptable presentation, such as a gelatin capsule. In particular, typically the core formulation of the present invention is preferably fabricated by compression into a tablet.

The resultant core formulation of the present invention is useful to treat diabetes mellitus. Surprisingly the resultant core formulation of the invention is as user friendly and clinically effective as compared to the administration of metformin alone or pioglitazone hydrochloride as demonstrated by co-administration of the two agents [Whitcomb; et al., U.S. Pat. No. 6,011,049], where in general, the incidence of adverse events was not influenced by age or menopausal status, and further, patients treated with the combination therapy attained better glycemic control than with either monotherapy.

It is to be understood, however, that for any particular subject being treated, e.g.; a mammal, specific dosage regimens should be adjusted according to the individual need. It is further to be understood that the dosages set forth herein are exemplary only and that they do not, to any extent limit the scope of the practice of the present invention.

The core formulation of the present invention may be administered orally, for example, with inert diluent or with an edible carrier. For the purpose of oral therapeutic administration, the core formulation may have excipients incorporated therein. The subject core formulation may also contain the following adjuvants: a binder such as microcrystalline cellulose, gum tragacanth or gelatin; an excipient such as starch or lactose, a disintegrating agent such as alginic acid, Primogel®, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring.

The subject core formulation of the invention may contain other various materials which modify the physical form of the dosage unit (the subject core formulation), for example, as coatings. Thus, the subject core formulation of the present invention may be coated with sugar, shellac or other enteric coating agents. Materials used in preparing these various compositions should be pharmaceutically pure and non-toxic in the amounts used.

In an alternative embodiment of the present invention. The resultant core formulation (having a first layer completely or partially covering the core), is treated whereby an outer shell, at least a portion of which comprises a biodegradable material having a predetermined rate of degradation or metabolism in the host being treated, is formed which encloses the particles of the first layer and/or the core.

The biodegradable material is a high molecular weight compound, which is physiologically acceptable and decomposes in the body of the human being or other animal and is absorbed.

The biodegradable material, comprising the outer shell, having a predetermined rate of degradation or metabolism or break down, is selected from those materials well known in the art, which do not react with metformin and/or pioglitazone hydrochloride. Such materials include, biodegradable polymers, such as polyorthoesters, polyanhydrides, polyamides based on glutamic acid, polyalkyl cyanoacrylates, polyesters of lactic and glycolic acid, polyactide polymers, cellulosic polymers, polyvinyl acetate, polyvinyl alcohol, polyvinylchloride, natural and synthetic rubbers, polyacrylates, polystyrene, etc. Additionally, reference is made to U.S. Pat. Nos. 4,166,800, and 4,389,330, which disclose additional shell forming materials and are incorporated hereinto by reference in their entirety.

The shell encapsulating the particles of pioglitazone hydrochloride of the first layer and/or the particles of metformin of the core is obtained by any conventional microencapsulation process whereby microspheres of metformin and/or pioglitazone hydrochloride are formed, e.g. a solvent removal process, a phase separation technique, coacervation etc. In this regard reference is made to U.S. Pat. Nos. 4,166,800 and 4,389,330, Conte et al, *J. Controlled Release*, vol. 26, (1993), pages 39–47; and U.S. Pat. No. 4,839,177; all of which are incorporated hereinto by reference in their entirety.

In a variation of the above alternative embodiment, the resultant core formulation is treated whereby only the top surface area of the first layer comprising metformin has a shell coating thereon. In this regard, reference is made to U.S. Pat. No. 5,916,584, incorporated hereinto by reference in its entirety, which describes the process for forming such a shell. The resulting core formulation having the first layer encapsulated by the shell comprising the shell material, is one which provides a delay time prior to release of the active ingredients, i.e. pioglitazone hydrochloride and metformin, to the patient being treated for diabetes mellitus.

It is to be understood that for either metformin or pioglitazone, any pharmaceutically acceptable form thereof can be employed. Such a form encompasses the free acids, free bases, salts and various hydrate forms, including semi-hydrate forms of these medicaments, as well as other-pharmaceutical materials which are used in the formulation process as acceptable excipient materials generally known to those skilled in the art.

It is understood that any one of the biguamide, i.e. drugs having the action of the stimulation of anaerobic glycolysis, is covered by this invention as these, like metformin, increase the sensitivity to insulin in peripheral tissues of the host, e.g. a human being or another animal. These compounds also are involved in the inhibition of glucose absorption from the intestine, suppression of hepatic gluconeogenesis, and inhibition of fatty acid oxidation. Examples of other typical biguamide included in this application are phenformin, buformin etc.

We claim:

1. A core formulation comprising,
   (a) a first layer comprising pioglitazone hydrochloride or a pharmaceutically acceptable salt thereof as active ingredient,
   (b) a core, at least a portion of which is enclosed by said first layer, comprising a biguamide as active ingredient.

2. The formulation as defined in claim 1 wherein said biguamide is metformin.

3. The formulation as defined in claim 2 wherein said pioglitazone hydrochloride is present in an amount ranging from 1 mg to 45 mg and, said metformin is present in an amount ranging from 10 mg to 4000 mg.

4. The formulation as defined in claim 2 which further comprises a biodegradable shell having a predetermined rate of degradation covering at least a portion of said first layer to provide a predetermined delay in the time period of release of at least said pioglitazone hydrochloride.

5. The formulation as defined in claim 2, wherein said pioglitazone hydrochloride and/or said metformin are present as biodegradable microspheres having a biodegradable shell coating and where said shell coating has a predetermined rate of degradation.

6. A method of administering pioglitazone hydrochloride and metformin to a mammal, which comprises treating the mammal with the formulation defined in claim 2.

7. A method for producing a controlled release formulation, which comprises:
   (a) producing a hollow outer shell comprising a biodegradable material having a predetermined rate of degradation to provide a predetermined delay in the time period of release of the contents destined to be enclosed by said shell;
   (b) inserting a core comprising metformin and having an outer layer comprising pioglitazone hydrochloride partially enclosing said core, into said hollow outer shell; and
   (c) sealing said core within said hollow outer shell.

8. A method of producing a combined formulation of pioglitazone hydrochloride and metformin, which comprises:
   (a) forming a core of the metformin; and
   (b) depositing a layer of pioglitazone hydrochloride on at least a portion of a surface of said core.

9. A method of treating diabetes mellitus in a patient in need thereof, which comprises administering to the patient the formulation of claim 1 wherein said active ingredients are each present in an effective amount.

10. A pharmaceutical composition in a single integral unit consisting essentially of an effective amount of pioglitazone hydrochloride combined with an effective amount of phenformin.

11. A pharmaceutical composition in a single integral unit consisting essentially of an effective amount of pioglitazone hydrochloride combined with an effective amount of buformin.

12. A method of treating diabetes mellitus in a patient in need thereof, which comprises, administering to the patient the integral composition of claim 10.

13. A method of treating diabetes mellitus in a patient in need thereof, which comprises, administering to the patient the integral composition of claim 11.

14. A method of treating diabetes mellitus in a patient in need thereof, which comprises, administering to the patient the composition of claim 1 wherein the biguamide is phenformin.

15. A method of treating diabetes mellitus in a patient in need thereof, which comprises, administering to the patient the composition of claim 1 wherein the biguamide is buformin.

* * * * *